US005942410A

United States Patent [19]
Lam et al.

[11] Patent Number: 5,942,410
[45] Date of Patent: Aug. 24, 1999

[54] COMPOSITION AND METHOD FOR STAINING CELLULAR DNA, COMPRISING THIAZINE DERIVATIVE METABISULFITE AND METHANOL OR ETHANOL

[75] Inventors: Paul Pong-Shing Lam, Vancouver; Peter William Payne, Surrey; David Michael Garner; Branko Palcic, both of Vancouver, all of Canada

[73] Assignee: Oncometrics Imaging Corp., Vancouver, Canada

[21] Appl. No.: 08/888,434

[22] Filed: Jul. 7, 1997

[51] Int. Cl.$^6$ .............. A61K 9/44; A61K 31/54; C12Q 1/68; G01K 33/53

[52] U.S. Cl. .............. 435/40.5; 435/6; 435/975; 514/224.8

[58] Field of Search .............. 514/224.8; 544/37; 435/6, 40.5, 575

[56] References Cited

U.S. PATENT DOCUMENTS

| | | |
|---|---|---|
| 4,998,284 | 3/1991 | Bacus et al. . |
| 5,016,283 | 5/1991 | Bacus et al. . |
| 5,109,429 | 4/1992 | Bacus et al. . |
| 5,281,517 | 1/1994 | Bacus et al. . |
| 5,432,056 | 7/1995 | Hartman et al. .......... 435/7.21 |
| 5,485,527 | 1/1996 | Bacus et al. . |

FOREIGN PATENT DOCUMENTS

| | | |
|---|---|---|
| 0 314 293 A2 | 3/1989 | European Pat. Off. . |
| 0445434 A2 | 9/1991 | European Pat. Off. . |

OTHER PUBLICATIONS

Dutt, M.K., "Use of Tris–Buffer–Fortified Thionine–SO$_2$ for Detection of DNA–Aldehyde Following Feulgen Procedure," *Microscopica Acta*, vol. 83, No. 4, Sep. 1980, pp. 311–316.

Störmer, V.U., et al., "Staining Properties and Applicability of Spectrally Pure Thionine and its Isomeres," *Acta histochem.*, vol. 70, 1982, pp. 161–172.

Dutta et al., "Efect of organic solvents on dye–DNA interaction", Indian Journal of Chemistry, Nov. 1986. vol. 25A, pp. 1001–1003.

Bulstra, S.K. et al., "Thionin Staining of Paraffin and Plastic Embedded Sections of Cartilage," *Biotechnic & Histochemistry*, vol. 68, No. 1, 1993, pp. 20–28.

Cooper, J.D., et al., "Accurate Counting of Neurons in Frozen Sections: Some Necessary Precautions," *J. Anatomy*, vol. 157, 1988, pp. 13–21.

Doudkine, A, et al., "Nuclear Texture Measurements in Image Cytometry," *Pathologica*, vol. 87, 1995, pp. 286–299.

Feulgen, R., et al., *Z. Physiol. Chem.* vol. 136, 1924, pp. 57–61.

Garner, D.M., et al., "CytoSavant and Its Use in Automated Screening of Cervical Smears," in Compendium on The Computerized Cytology and Histology Laboratory, Wied, G.L., et al., eds., Tutorials of Cytology, Chicago, 1994.

Humason, Gretchen L., Animal Tissue Techniques, 4th Ed., W.H. Freeman & Company, San Francisco, 1979, pp. 154–155, 181–183, 208, 316–319, 432–433, 471–473.

Insausti, R., et al., "The Human Entorhinal Cortex: A Cytoarchitectonic Analysis," *The Journal of Comparative Neurology*, vol. 355, 1995, pp. 171–198.

Jaggi, B., et al., "Design of a Solid–State Microscope," *Optical Engineering*, Jun. 1989, vol. 28 No. 6, pp. 675–682.

Jaggi, B., et al., "The Design and Development of an Optical Scanner for Cell Biology," *IEEE Proceedings Engineering in Medicine and Biology Society*, vol. 2, sep. 1985; pp. 980–985.

Kutscher, Charles L., et al., "Hematoxylin and Thionin Techniques for Staining Myeline and Cells: Variations and Critical Steps," *Brain Research Bulletin*, vol. 19, 1987, pp. 161–163.

Mikel, Ulrika V., et al., "A Comparative Study of Quantitative Stains for DNA in Image Cytometry," *Analytical and Quantitative Cytology and Histology*, vol. 13, No. 4, Aug. 1991, pp. 253–260.

Muto, Tetsuichiro, et al., "Mucin Abnormality in Colonic Mucosa in Patients with Familial Polyposis Coli," *Seminars in Surgical Oncology*, vol. 3, 1987, pp. 179–182.

Ota, H., et al., "A Dual Staining Method for Identifying Mucins of Different Gastric Epithelial Mucous Cells," *Histochemical Journal*, vol. 23, 1991, pp. 22–28.

Poon, S.S.S., et al., "Cell Recognition Algorithms for the Cell Analyzer," *IEEE Proceedings Engineering in Medicine and Biology Society*, vol. 4, Nov. 1987; pp. 1454–1456.

Schulte, E., et al., "The Influence of Cationic Thiazine Dyes on Eosin Y–Uptake of Red Blood Cells in Romanowsky–Giemsa Type," *Acta Histochemica*, Suppl.–Band XXXVII, S., 1989, pp. 139–147.

Schulte, Erik, M.D., "Air Drying as a Preparatory Factor in Cytology: Investigation of its Influence on Dye Uptake and Dye Binding," *Diagnostic Cytopatholgy*, vol. 2, No. 2, Apri.–Jun. 1986, pp. 160–167.

Schulte, Erik, M.D., et al., "Standardization of the Papanicolaou Stain: I. A Comparison of Five Nuclear Stains," *Analytical and Quantitative Cytology and Histology*, vol. No. 3, Jun. 1990, pp. 149–156.

Tolivia, J., et al., "Differential Technique to Stain Nerve Cells and Fibers in Methacrylate Sections," *The Anatomical Record*, vol. 217, 1987, pp. 318–320.

(List continued on next page.)

*Primary Examiner*—Sandra E. Saucier
*Assistant Examiner*—Vera Afremova
*Attorney, Agent, or Firm*—Christensen O'Connor Johnson & Kindness PLLC

[57] ABSTRACT

A composition and method for staining cellular DNA are disclosed. The composition of the present invention is an aqueous alcoholic solution that includes a cationic stain, a metabisulfite, and an alcohol preferably selected from methanol, ethanol, and mixtures thereof. In a preferred embodiment, the cationic stain is thionin.

24 Claims, No Drawings

OTHER PUBLICATIONS

Tolivia, J., et al., "Differential Thionin Block Staining of Nerve Cells and Fibers for Paraffin–Embedded Material in Mammalian Central Nervous System,"*Neuroscience Letters,* vol. 102, 1989, pp. 155–158.

Van Duijn, P., "A Histochemical Specific Thionine–$SO_2$ Reagent and its Use in a Bi–Color Method for Deoxyribonucleic Acid and Periodic Acid Schiff Positive Substances," *J. Histochem. Cytochem.,* vol 4, 1956, pp. 55–63.

Winzek, C., et al., "An Improved Method to Investigate Staining Kinetics in Single Cells," Histochemistry, vol. 86, 1987, pp. 421–426.

Winzek, C., et al., "Staining Kinetics in Single Cells: Part II. Diffusion Processes Inside the Cell," *Histochemistry,* vol. 90, 1988, pp. 79–83.

COMPOSITION AND METHOD FOR STAINING CELLULAR DNA, COMPRISING THIAZINE DERIVATIVE METABISULFITE AND METHANOL OR ETHANOL

FIELD OF THE INVENTION

The present invention generally relates to a composition and method for staining cellular DNA, and more particularly, to a composition that includes a cationic stain and methods for its use.

BACKGROUND OF THE INVENTION

Image cytometry has been increasingly used in cytopathology and histopathology to detect aneuploid cell populations within preneoplastic or neoplastic lesions. DNA image cytometry has gained wide acceptance in pathology and cytopathology as a means to obtain diagnostic and prognostic information for human cancer. Such diagnoses require the accurate determination of cellular DNA content. Accordingly, various methods for quantitatively staining nuclear DNA have been developed. The reproducibility and reliability of several quantitative DNA stains has been recently reported. "A Comparative Study of Quantitative Stains for DNA in Image Cytometry," Mickel, U. V. and Becker, Jr., R. L., *Analytical and Quantitative Cytology and Histology* 1991, 13:253–260.

Included among the various techniques for staining cellular DNA are Feulgen staining techniques. Feulgen, R. and Voit K., *Z. Physiol. Chem.* 1924, 136:57–61. Feulgen discovered that hydrolysis of fixed tissues (i.e., DNA hydrolysis) exposed the deoxypentose present in cell nuclei in an aldehyde form. Subsequently, Feulgen found that the mild acid hydrolysis of cellular DNA followed by the addition of a Schiff reagent provided a reddish-purple color to DNA-containing structures. The Feulgen technique continues to be practiced as a method for quantitating cellular DNA and generally involves the steps of oxidizing nucleic acids to provide aldehydes, and reacting these aldehydes with a Schiff reagent to form a purple-red color indicative of the presence of DNA. Because the reaction is stoichiometric, the intensity of the color is directly related to the amount of DNA in the sample, provided that excess reagents are washed out.

In 1954, a thionin-sulfite reagent was found to exclusively stain nuclei of hydrolyzed sections of mouse kidney and liver cell nuclei. Van Duijn, P., *J. Histochem. Cytochem.* 1956, 4:55–63. The aldehyde reagent contained thionin and sulfur dioxide in a medium of t-butanol and water. This thionin reagent was prepared by acidifying a solution of thionin in aqueous t-butanol (water:t-butanol, 1:1) with aqueous hydrochloric acid followed by the addition of sodium metabisulfite. Van Duijn concluded from the histochemical data that the thionin-sulfite/t-butanol reagent contains one or more components that react with aldehydes, although the exact chemical nature of the reaction between thionin and sulfur dioxide and the nucleic acids was unclear. The use of Feulgen staining methods has continued to present, and various compounds have been used as Feulgen stains. Thionin, generally regarded as a nuclear stain, is one of the more commonly used stains in the Feulgen procedure.

Despite the many years that have passed since the original report of the thionin-Feulgen stain reagent, the composition of the reagent has remained unchanged (i.e., a solution of thionin and sodium metabisulfite in aqueous t-butanol adjusted to about pH 1.5 with aqueous hydrochloric acid).

Although the Feulgen thionin staining method developed in the 1950s does facilitate quantitative DNA measurements, the use of t-butanol as a solvent for the traditional thionin staining reagent is not without its drawbacks. First, t-butanol is an irritating substance and presents a work hazard. Second, because t-butanol has a melting point of about 25° C., it is often a solid at room temperature and requires heating and melting so that it may be dispensed as a liquid in the preparation of the reagent. Unlike most other low molecular weight alcohols, t-butanol is difficult to dispose of properly. Because of its hazardous nature, there are also shipping restrictions associated with t-butanol. In contrast to other simple alcohols, t-butanol is extremely expensive (e.g., $45 per liter compared to methanol or ethanol at about $2 per liter). Perhaps most importantly, the useful shelf life of thionin/t-butanol staining solutions is about two days. Such a short shelf life precludes the storage and therefore commercial utility of such a reagent, and requires one who wishes to use the thionin reagent in a Feulgen staining method to prepare the reagent immediately prior to use.

Accordingly, there exists a need for a thionin-based reagent that offers the advantages of cellular DNA quantitation afforded by the traditional thionin/t-butanol staining reagent without the accompanying disadvantages associated with t-butanol, a key component of the reagent. More specifically, there exists a need for a thionin staining reagent that has a long and stable shelf life. The present invention seeks to fulfill these needs and provides further related advantages.

SUMMARY OF THE INVENTION

In one aspect, the present invention provides a composition that is useful for staining cellular DNA. Generally, the composition is an aqueous alcoholic solution that includes a cationic stain having a formula:

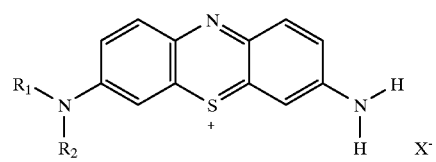

where $R_1$ and $R_2$ are independently selected from hydrogen and methyl, and X is a counterion; a metabisulfite; and an alcohol selected from either methanol ethanol, and mixtures of methanol and ethanol. In a preferred embodiment, the cationic stain is thionin acetate (i.e., $R_1$ and $R_2$ are hydrogen and X is acetate).

In another aspect of the present invention, a method for staining cellular DNA is provided. In the method, the composition noted above is applied to a cell to provide a cell having a stained nucleus. The present invention also provides a method for quantitating cellular DNA that includes the steps of staining the cell with the composition noted above to provide a cell having a stained nucleus, and then measuring the optical density of the stain nucleus to determine the presence or amount of DNA present in the nucleus.

In still another aspect, the present invention provides a kit for staining cellular DNA that includes the composition noted above.

DETAILED DESCRIPTION OF THE PREFERRED EMBODIMENT

The present invention generally relates to a composition and method for staining cellular DNA. More specifically, the present invention provides a composition that is useful as a reagent in a Feulgen staining method and useful in both staining and determining the presence or amount of cellular DNA. The composition of the present invention is an aqueous alcoholic solution that includes a cationic dye, a metabisulfite, and an alcohol preferably selected from methanol, ethanol, and mixtures of ethanol and methanol.

The cationic stain useful in the composition of the present invention is a phenothiazine derivative, and more specifically, a 3,7-diamino-5-phenothiazine derivative. The cationic stain is represented by the following formula:

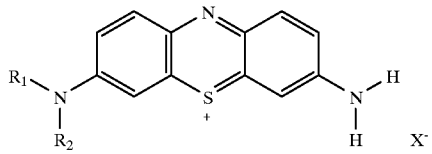

where $R_1$ and $R_2$ are either hydrogen, methyl, or combinations of hydrogen and methyl, and X is a counterion. While the cationic stain useful in the composition of the present invention is represented by the formula above, it will be appreciated that the cationic stain may also be represented by other equivalent formulas including:

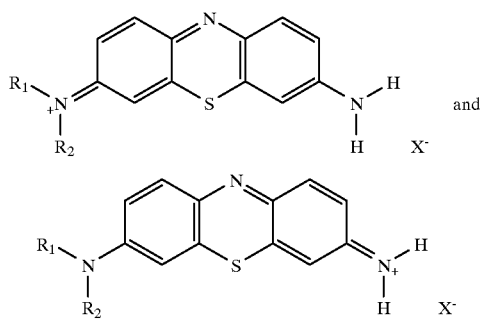

Suitable cationic stains include Azure A ($R_1$ and $R_2$ are methyl) and Azure C ($R_1$ is methyl and $R_2$ is hydrogen). In a preferred embodiment, the cationic stain is thionin ($R_1$ and $R_2$ are hydrogen). Suitable counterions X include anions that do not adversely affect the performance of the cationic stain in the staining procedure and include acetate, chloride, and bromide. In a preferred embodiment, the counterion is acetate. In a particularly preferred embodiment, the cationic stain is thionin acetate ($R_1$ and $R_2$ are hydrogen and X is acetate).

The cationic stain is present in the composition at a concentration from about $1.0 \times 10^{-3}$ M to about $2.5 \times 10^{-2}$ M, and preferably from about $4.0 \times 10^{-3}$ M to about $8.0 \times 10^{-3}$ M.

In addition to the cationic stain, the composition of the present invention also preferably includes a metabisulfite. While embodiments of the present invention that include bisulfite are useful as staining solutions, it has been found that metabisulfite containing solutions provide the best staining results. Suitable metabisulfites do not adversely affect the staining performance of the composition of the present invention. Suitable metabisulfites include metal metabisulfites such as lithium, sodium, and potassium metabisulfites. Preferably, the composition includes either sodium or potassium metabisulfite. Preferably, the metabisulfite is present in the composition at a concentration from about $1.0 \times 10^{-3}$ M to about $2.5 \times 10^{-2}$ M, and preferably from about $4.0 \times 10^{-3}$ M to about $8.0 \times 10^{-3}$ M. In contrast to Feulgen staining solutions known in the art that have a molar ratio of metabisulfite:thionin of 4–10:1, in the composition of the present invention, a molar metabisulfite:thionin ratio of 1:1 is preferred.

The composition of the present invention includes a cationic stain and a metabisulfite in aqueous alcohol. The aqueous alcohol solution serves to solubilize the stain and metabisulfite as well as any active DNA staining components formed in the solution. Therefore, the alcohol is preferably miscible with water and, for ease of reagent preparation, a liquid at room temperature. Alcohols useful in the composition include C1 to C3 alcohols (i.e., methanol, ethanol, n-propanol and isopropanol), and mixtures of these alcohols. Preferred alcohols include methanol, ethanol, and mixtures of methanol and ethanol. Preferably, the aqueous alcohol solution contains from about 20 to about 60 percent alcohol, and more preferably, about 40 percent alcohol. The composition of the present invention is preferably an aqueous acidic solution having a pH of from about 1.0 to about 2.0, and more preferably, from about 1.3 to about 1.5. While the pH of the composition can be adjusted with any one of a number of acids, the pH of the solution is preferably adjusted with aqueous hydrochloric acid.

The preparation of a representative composition of the present invention, a thionin/methanol staining solution, is described in Example 1.

Generally, the reaction of the above-noted cationic stain with metabisulfite results in the formation of an active ingredient that binds to hydrolyzed DNA. Thus, the composition of the present invention is useful for staining cellular DNA. Accordingly, in another aspect, the present invention provides a method for staining cellular DNA. In the method, the composition described above is applied to cells to provide cells having stained nuclei. Basic procedures, such as cell fixation, dehydration, clearing, staining, and mounting, as well as specific staining methods, including Feulgen techniques, nucleic acid staining, and the staining of cellular elements, are well known to those of skill in the art. Basic cytological and histochemical techniques are described in *Histological and Histochemical Methods: Theory and Practice,* 2nd Ed., J. A. Kierenan, ed., Pergamon Press, New York, 1990, and *Animal Tissue Techniques* 4th Ed., Gretchen L. Humason, W.H. Freeman & Company, San Francisco, 1979, both expressly incorporated herein by reference.

As noted above, the method of the present invention includes applying the composition described above to cells. The composition and method of the present invention are useful in staining virtually any cell having a nucleus including, for example, epithelial, muscle, nerve, and connective tissue cells. Any one of a number of cell preparations may be used in the method, for example, preparations of cells of interest include conventional smears, histological preparations, and monolayer preparations. Generally, cells are deposited on a microscope slide for staining. After deposit on the slide, the cells are fixed by immersing the slide in a fixative solution and then rinsed. Alternatively, fixed cells may also be deposited on the slide for staining. After rinsing, the cellular DNA is then hydrolyzed by immersing the slides in an acidic solution. Following another rinse, the cells are stained by immersing the slides in a staining solution. After additional rinses, the cells are then dehydrated by immersion in ethanol solutions, followed by clearing in xylene. At this point, the staining results may be visualized by any one of a number of techniques including manual and automated techniques including, for example, microscopic and image cytometric techniques. A detailed method for a representative staining procedure that includes the method of the present invention is described in Example 1. Although the staining procedure may be a manual procedure, the method of the present invention may also be incorporated into an automated staining procedure.

Because the staining method of the present invention is a quantitative method for staining cellular DNA, the combination of the steps of staining cells with the staining solution of the present invention and measuring the optical density of the resulting stained nuclei permits the determination of the presence or amount of DNA present in a cell's nucleus. Thus, in another aspect, the present invention provides a method for quantitating cellular DNA that includes the steps of staining the cell with the composition described above, and then measuring the optical density of the stained nuclei to determine either the presence or the amount of DNA present in the nucleus. The optical densities of stained nuclei may be measured by manual and automated techniques including, for example, optical scanners, microscopes, and other image cytometers. Suitable instruments for measuring the optical densities of stained cells are known in the art and include those described in "The Design and Development of an Optical Scanner for Cell Biology," Jaggi, B. and Palcic, B., *IEEE Proc. Eng. Med. Biol.* 1985; 2:980–985; "Cell Recognition Algorithms for the Cell Analyzer," Jaggi, B. and Palcic B., *IEEE Proc. Eng. Med. Biol.* 1987; 4:1454–1456; and "Design of a Solid State Microscope," Jaggi, B., Deen, M. J., and Palcic B., *Opt. Engineer* 1989; 28(6):7675–682, each expressly incorporated herein by reference.

The methods of the present invention are useful in techniques in which stained cells are digitally imaged and the resulting digital intensity images manipulated by computer to perform a variety of cell feature measurements. Cellular features, such as the size, shape, and DNA content of the nucleus, and other features that describe the spatial distribution of chromatin within the nucleus, can be calculated. Features that describe the chromatin distribution are collectively referred to as texture features, and texture features can be selected for their ability to differentiate between the various descriptive classes of chromatin patterns and to further provide quantitative information regarding the extent of changes in chromatin patterns associated with certain diseases including, for example, malignancy. Thus, the composition and methods of the present invention are useful in nuclear texture measurements, and consequently the diagnosis and prognosis of certain diseases. Nuclear texture measurements in image cytometry and their utility in the diagnosis and prognosis of human cancer are described in A. Doudkine, C. MacAulay, N. Poulin, and B. Palcic, "Nuclear Texture Measurements in Image Cytometry," *Pathologica* 1995; 87:286–299, expressly incorporated herein by reference.

The integrated optical density (IOD), a nuclear feature measurement, for cells stained by representative staining solutions of the present invention and the traditional thionin/t-butanol stain are presented in Example 3.

As noted above, one of the most significant drawbacks to the traditional thionin/t-butanol Feulgen staining technique is the short shelf life of the t-butanol-based staining solution. In contrast, the methanol- and ethanol-based compositions of the present invention have considerable and significantly longer shelf life. A comparison of the staining performance of representative compositions of the present invention (i.e., thionin/methanol and thionin/ethanol staining solutions) and the traditional Feulgen staining reagent (i.e., thionin/t-butanol staining solution) is described in Example 2. The results summarized in Tables 1 and 2 clearly demonstrate that (1) the composition of the present invention provides cellular DNA staining comparable to the standard thionin/t-butanol staining solution, and (2) the ability of the composition of the present invention to effectively stain cellular DNA remains essentially constant over a period of about five weeks. In contrast, the conventional thionin/t-butanol staining solution loses about 40 percent of its staining capacity in only four days. The enhanced stability of the composition of the present invention compared to the conventional staining solution offers significant practical and commercial advantages. For example, while the conventional staining solution must be freshly prepared immediately prior to staining by the practitioner or clinician, the composition of the present invention, by virtue of their stability and long shelf life, may be prepared, stored, and used repeatedly over a relatively long period of time.

The utility and success of the composition and method of the present invention in quantitatively staining intracellular DNA is noteworthy in view of the well established sensitivity of quantitative DNA methods to various chemical treatments. Quantitative DNA measurements are known to be highly sensitive to, for example, cell fixation methods. Fixation methods, and more specifically the reagents and solvents used in a particular method, have been shown to dramatically affect intracellular DNA quantitation. The variation in the amount of cellular DNA available for staining has been suggested as one reason for the variation observed in certain methods. Within a cell, DNA is associated with protein. Cell fixation serves, in part, to denature the associated protein and to expose the DNA thus making the DNA available for staining. Fixation methods typically employ solvents, including alcohols, to effect protein denaturation. Generally, the extent to which the associated protein is denatured, and the extent to which DNA is made available for measurement, is highly dependent on the reagents and methods employed. For instance, in formalin fixation methods, the concentration of alcohol in the fixation reagent has been found to have a critical effect on protein denaturation and, consequently, the quantitative measurement of intracellular DNA. In general, the effect of a specific solvent or reagent on a quantitative DNA method is largely unpredictable and may typically be determined empirically through experimentation.

Despite the well-known sensitivity of quantitative DNA methods to various reagents and solvents, the composition and method of the present invention have been found to be effective in quantitating intracellular DNA. As demonstrated by the staining results presented in Examples 2 and 3, the present composition is as effective in staining intracellular DNA as the standard t-butanol-based composition. Furthermore, the present composition provides a staining reagent that has a stable shelf life considerably greater than the standard staining composition.

Accordingly, in another aspect, the present invention provides a kit for staining cellular DNA. The kit of the present invention includes the composition described above. Generally, composition components are contained in one or more vessels in the kit. For example, in one embodiment, the kit includes a staining reagent that incorporates all of the components of the composition of the present invention in a single solution (i.e., an aqueous alcoholic solution of a cationic dye and a metabisulfite adjusted to about pH 1.5). Alternatively, in another embodiment, the kit includes a staining reagent in dry (i.e., powdered) form. In such an embodiment, the kit can contain solid cationic stain in one vessel and solid metabisulfite in a second vessel. For this embodiment, the liquid components of the composition are added to the dry reagents which are then combined to provide the staining solution of the invention. In yet another embodiment, the kit can include a combination of solid cationic stain and metabisulfite in a single vessel.

In addition to the staining reagent, the kit also includes a rinse reagent (i.e., an aqueous acidic solution of metabisulfite). As noted above for the staining reagent, the rinse reagent may be provided as a solid or in solution. The kit can optionally include unstained, cultured cells on microscope slides (control slides) to, for example, monitor quality control of the staining procedure. The kit can also include an instruction booklet that provides directions for the staining procedure and, for applicable embodiments, directions for preparing the staining solution from the kit's reagents.

The following examples are provided for the purposes of illustration, and not limitation.

EXAMPLES

Example 1

Representative Procedure for Cellular DNA Staining

In this example, a representative procedure for staining cellular DNA with alcohol solutions of thionin is described. The reagents used in the DNA staining procedure, including methanol and t-butanol solutions of thionin, and fixative and rinse solutions, were prepared as described below.

Stain Reagent Preparations:
A. Representative Staining Solution of Present Invention
Thionin/methanol Staining Solution
1. Add 0.5 g thionin (Aldrich Chemical Co., Milwaukee, Wis.) and 0.5 g sodium metabisulfite to a 500 ml glass bottle with a stirring bar.
2. Add 200 ml methanol. Mix well.
3. Add 250 ml distilled water.
4. Add 50 ml 1N hydrochloric acid and cap the bottle.
5. Stir stain solution for one hour. Protect solution from light by wrapping the bottle with aluminum foil. Do not refrigerate.
6. Filter stain solution through filter paper (No. 1 grade) in a fume hood immediately prior to use.

B. Conventional Feulgen Staining Solution
Thionin/t-butanol Staining Solution
1. Add 0.5 g thionin to 435 ml distilled water in a 2000 ml Erlenmeyer flask.
2. Heat solution to boiling for about 5 minutes and then allow to cool to about room temperature.
3. Add 435 ml t-butanol. (If necessary, melt the t-butanol in a waterbath. The melting point of t-butanol is 25–26° C. and therefore is a solid at temperatures below about 25° C.).
4. Add 130 ml 1N aqueous hydrochloric acid.
5. Add 8.7 g sodium metabisulfite.
6. Add stirring bar and seal container with Parafilm M.
7. Stir stain solution for at least 1 hour. Protect from light and do not refrigerate.
8. Filter stain solution through filter paper (No. 1 grade) in a fume hood just prior to use.

Other Reagent Preparations:
Bohm-Sprenger Fixative
1. Combine 320 ml methanol and 60 ml aqueous formaldehyde (37%) in a 500 ml glass bottle.
2. Add 20 ml glacial acetic acid.
3. Mix well and seal with Parafilm M.

Rinse Solution
1. Dissolve 7.5 g sodium metabisulfite in 1425 ml distilled water in a 2000 ml Erlenmeyer flask.
2. Add 75 ml 1N aqueous hydrochloric acid.
3. Add stirring bar and stir until dissolved. Seal flask with Parafilm M.

1% Acid Alcohol
1. Mix 280 ml of absolute ethanol and 120 ml distilled water.
2. Add 4 ml concentrated hydrochloric acid.
3. Mix well.

The reagents prepared as described above were then used to stain cellular DNA by the following method. Preparations of cells of interest (e.g., cells from uterine cervix samples), including conventional smears and monolayer preparations, may be used in the method. In the method, cells are generally deposited on a microscope slide for staining.

Staining Procedure:
1. Deposit cells on a microscope slide.
2. Fix cells by immersing slide in Bohm-Sprenger fixative: 30–60 minutes.
3. Rinse slide in distilled water: 1 minute, agitate.
4. Hydrolyze cellular DNA by immersing slide in 5N hydrochloric acid: 60 minutes at room temperature.
5. Rinse slides in distilled water: 15 dips, agitate.
6. Stain cells by applying freshly filtered thionin stain solution: 75 minutes.
7. Wash slides in distilled water: 6 changes, 20 dips each.
8. Rinse slides in freshly prepared rinse solution: 3 changes: 30 seconds for the first two rinses, 5 minutes for the last rinse.
9. Rinse slides in distilled water: 3 changes, 20 dips each.
10. For mucoidal samples only:
    Optionally rinse slides in 1% acid alcohol: 2 minutes.
11. Rinse slides in distilled water: 3 changes, 20 dips each.
12. Dehydrate cells by sequentially immersing the slides in 50%, 75% aqueous ethanol and two changes of 100% ethanol: 1 minute each.
13. Clear slides by immersing in xylene: 5 minutes.
14. Mount coverslips on slides.
15. Identify slides with barcode labels if desired.

Example 2

Cellular DNA Staining Results: Performance Over Time

This example compares the cellular DNA staining performance of thionin/methanol and thionin/t-butanol staining solutions over time. In the comparative study, thionin solutions were prepared in either methanol or t-butanol, as described in Example 1 above, and cellular preparations were stained and the optical densities of the stained nuclei measured. To determine the effect of time on the performance of each thionin staining solution, cellular stainings with each thionin solution were performed at regular time intervals (see Table 1 below) with the same stock staining solution. In effect, the comparative experiment determined the useful shelf life of each of the specific thionin staining reagents studied.

Cellular preparations (HL-60 cells from American Type Culture Selection) were stained by the procedure described in Example 1 above. The integrated optical density (IOD) for each sample was determined by quantitative image cytometry using an optical scanner and by the methods described in "CytoSavant and Its Use in Automated Screening of Cervical Smears," Garner, D. M., Harrison, A., MacAulay, C., and Palcic, B., in *Compendium on the Computerized Cytology and Histology Laboratory*, Wied, G. L., Bartels, P. H., Rosenthal, D. L., and Schenck, U., eds., Tutorials of Cytology, Chicago, 1994; "The Design and Development of an Optical Scanner for Cell Biology," Jaggi, B. and Palcic, B., *IEEE Proc. Eng. Med. Biol.* 1985; 2:980–985; "Cell Recognition Algorithms for the Cell Analyzer," Jaggi, B. and Palcic B., *IEEE Proc. Eng. Med. Biol.* 1987; 4:1454–1456; and "Design of a Solid State Microscope," Jaggi, B., Deen, M. J., and Palcic B., Opt. Engineer 1989; 28(6):7675–682, all expressly incorporated herein by reference. For each data point, three slides were stained followed by the measurement of their optical density. The performance (i.e., the capacity to stain cellular DNA and provide optically dense nuclei) of the two thionin staining solutions is summarized in Table 1 below.

|     | Thionin Solution | | |
| --- | --- | --- | --- |
| Day | t-Butanol | Methanol | Ethanol |
| 0 | 114.7 ± 4.2 | 120.0 ± 2.0 | 120.9 ± 1.6 |
| 1 | 117.3 ± 3.5 | — | — |
| 2 | 123.0 ± 5.7 | — | — |
| 3 | 85.3 ± 3.1 | — | — |
| 4 | 68.3 ± 4.7 | — | — |
| 7 | — | 119.7 ± 3.1 | 116.2 ± 5.6 |
| 14 | — | 119.3 ± 2.1 | 118.9 ± 1.2 |
| 21 | — | 117.7 ± 2.5 | 113.3 ± 3.3 |
| 28 | — | 119.7 ± 2.1 | 106.5 ± 1.8 |
| 35 | — | 112.0 ± 2.0 | 114.4 ± 6.0 |

As shown in Table 1, the performance of the t-butanol-based thionin staining solution decreases dramatically and rapidly over time. After only four days, the effectiveness of this solution, as measured by the optical density of cells stained, has decreased to about 60% of its original value. In contrast, the performance of the thionin/methanol and thionin/ethanol staining solutions remains essentially unchanged over a period of four weeks. These results demonstrate that methanolic and ethanolic solutions of thionin are significantly more stable than solutions of thionin in t-butanol. The results also demonstrate the effectiveness and comparability of methanol and ethanol as solvents for thionin staining, and their superiority to t-butanol as a thionin stain solvent.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A composition comprising a cationic stain having the formula:

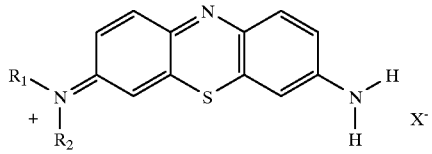

wherein $R_1$ and $R_2$ are independently selected from the group consisting of hydrogen and methyl, and X is a counterion;
a metabisulfite; and an aqueous alcoholic solution comprising an alcohol selected from the group consisting of methanol, ethanol, and mixtures thereof.

2. The composition of claim 1 wherein $R_1$ and $R_2$ are hydrogen.

3. The composition of claim 1 wherein $R_1$ is methyl and $R_2$ is hydrogen.

4. The composition of claim 1 wherein X is selected from the group consisting of acetate, chloride, and bromide.

5. The composition of claim 1 wherein X is acetate.

6. The composition of claim 1 wherein $R_1$ and $R_2$ are hydrogen and X is acetate.

7. The composition of claim 1 wherein the cationic stain is present in the composition at a concentration of from about $1.0 \times 10^{-3}$ M to about $2.5 \times 10^{-2}$ M.

8. The composition of claim 1 wherein the cationic stain is present in the composition at a concentration of from about $4.0 \times 10^{-3}$ M to about $8.0 \times 10^{-3}$ M.

9. The composition of claim 1 wherein the metabisulfite is selected from the group consisting of lithium, sodium, and potassium metabisulfites.

10. The composition of claim 1 wherein the metabisulfite is present in the composition at a concentration of from about $1.0 \times 10^{-3}$ M to about $2.5 \times 10^{-2}$ M.

11. The composition of claim 1 wherein the metabisulfite is present in the composition at a concentration of from about $4.0 \times 10^{-3}$ M to about $8.0 \times 10^{-3}$ M.

12. The composition of claim 1 wherein the composition has a pH of from about 1.0 to about 2.0.

13. The composition of claim 1 wherein the composition has a pH of from about 1.3 to about 1.5.

14. A method for staining cellular DNA comprising applying a staining solution to a cell to provide a cell having a stained nucleus, wherein the staining solution comprises a cationic stain having the formula:

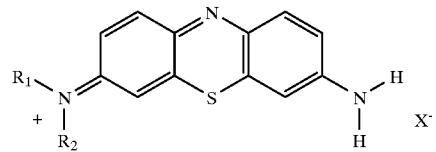

wherein $R_1$ and $R_2$ are independently selected from the group consisting of hydrogen and methyl, and X is a counterion;
a metabisulfite; and an aqueous alcoholic solution comprising an alcohol selected from the group consisting of methanol, ethanol, and mixtures thereof.

15. The method of claim 14 wherein $R_1$ and $R_2$ are hydrogen.

16. The method of claim 14 wherein $R_1$ is methyl and $R_2$ is hydrogen.

17. The method of claim 14 wherein X is selected from the group consisting of acetate, chloride, and bromide.

18. The method of claim 14 wherein $R_1$ and $R_2$ are hydrogen and X is acetate.

19. The method of claim 14 wherein the cationic stain is present in the composition at a concentration of from about $1.0 \times 10^{-3}$ M to about $2.5 \times 10^{-2}$ M.

20. The method of claim 14 wherein the metabisulfite is selected from the group consisting of lithium, sodium, and potassium metabisulfites.

21. The method of claim 14 wherein the metabisulfite is present in the composition at a concentration of from about $1.033 \; 10^{-3}$ M to about $2.5 \times 10^{-2}$ M.

22. The method of claim 14 wherein the composition has a pH of from about 1.0 to about 2.0.

23. A method for quantitating cellular DNA comprising:
staining the cell with a composition to provide a cell having a stained nucleus, wherein the composition comprises a cationic stain having the formula:

11

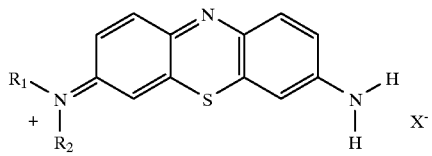

wherein $R_1$ and $R_2$ are selected from the group consisting of hydrogen and methyl, and X is a counterion;

a metabisulfite; and an aqueous alcoholic solution comprising an alcohol selected from the group consisting of methanol, ethanol, and mixtures thereof; and measuring the optical density of the stained nucleus as an indication of the presence or amount of DNA present in the nucleus.

24. A kit for staining cellular DNA comprising a cationic stain having the formula:

12

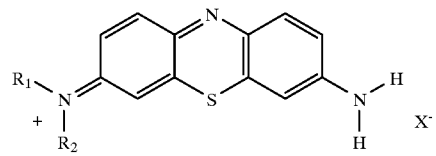

wherein $R_1$ and $R_2$ are selected from the group consisting of hydrogen and methyl, and X is a counterion;

a metabisulfite; and an aqueous alcoholic solution comprising an alcohol selected from the group consisting of methanol, ethanol, and mixtures thereof;

wherein the cationic stain, metabisulfite, and alcohol are contained in one or more vessels.

* * * * *

UNITED STATES PATENT AND TRADEMARK OFFICE
CERTIFICATE OF CORRECTION

PATENT NO. : 5,942,410
DATED : August 24, 1999
INVENTOR(S) : P.P.-S. Lam et al.

It is certified that error appears in the above-identified patent and that said Letters Patent is hereby corrected as shown below:

On the title page item,

| | | |
|---|---|---|
| [56]<br>Pg. 1,<br>col. 1 | Refs. Cited<br>(Other Publs.,<br>Item 3) | "Efect" should read --Effect-- |
| [56]<br>Pg. 1,<br>col. 1 | Refs. Cited<br>(Other Publs.,<br>Item 17) | "*Cytopatholgy*" should read --*Cytopathology*-- |
| 10<br>(Claim 21, | 61<br>line 3) | "1.033 10$^{-3}$" should read --1.0x10$^{-3}$-- |

Signed and Sealed this

Thirtieth Day of January, 2001

Attest:

Attesting Officer

Q. TODD DICKINSON

Director of Patents and Trademarks